US010218111B2

(12) United States Patent
Schüttler et al.

(10) Patent No.: US 10,218,111 B2
(45) Date of Patent: Feb. 26, 2019

(54) IMPLANTABLE PLUG CONNECTOR

(71) Applicant: c/o CorTec GmbH, Freiburg (DE)

(72) Inventors: Martin Schüttler, Emmendingen (DE); Julia Koch, Freiburg (DE); Juan Sebastian Ordonez, Freiburg (DE); Jörn Rickert, Freiburg (DE)

(73) Assignee: CORTEC GMBH, Freiburg (DE)

( * ) Notice: Subject to any disclaimer, the term of this patent is extended or adjusted under 35 U.S.C. 154(b) by 0 days.

(21) Appl. No.: 15/582,053

(22) Filed: Apr. 28, 2017

(65) Prior Publication Data

US 2017/0237199 A1 Aug. 17, 2017

Related U.S. Application Data

(63) Continuation of application No. PCT/EP2015/075286, filed on Oct. 30, 2015.

(30) Foreign Application Priority Data

Oct. 30, 2014 (DE) .................. 10 2014 115 859

(51) Int. Cl.
*H01R 13/22* (2006.01)
*H01R 13/52* (2006.01)
(Continued)

(52) U.S. Cl.
CPC ......... *H01R 13/5224* (2013.01); *A61N 1/375* (2013.01); *H01R 13/22* (2013.01);
(Continued)

(58) Field of Classification Search
CPC .... H01R 13/22; H01R 13/24; H01R 13/2407; H01R 13/2414; H01R 13/2424; H01R 13/2464; H01R 13/5224; H01R 12/714
See application file for complete search history.

(56) References Cited

U.S. PATENT DOCUMENTS 4,891,013 A * 1/1990 Komaki ............... G06K 7/0021
200/512
5,074,799 A * 12/1991 Rowlette, Sr. ......... H01R 13/22
439/178
(Continued)

FOREIGN PATENT DOCUMENTS

| DE | 196 22 669 A1 | 12/1997 |
|---|---|---|
| WO | 2013/048396 A1 | 4/2013 |

OTHER PUBLICATIONS

International Search Report issued for corresponding International Application No. PCT/EP2015/075286 dated Apr. 14, 2016.
(Continued)

*Primary Examiner* — Felix O Figueroa
(74) *Attorney, Agent, or Firm* — Myers Wolin, LLC

(57) ABSTRACT

An implantable plug connector is provided, an inner portion of which has a number of contact surfaces which are embedded in a surface of a first substrate. An outer portion of the implantable plug connector has a number of contact surfaces embedded in at least one surface of a second substrate. The outer portion defines a space, in which the inner portion can be received in a mounting state, where, in a pre-mounting state, the contact surfaces are set back with respect to the surface of the respective substrate, and where, in a mounting state, the inner portion is pressed against the outer portion such that mutually corresponding contact surfaces come into contact with each other.

16 Claims, 8 Drawing Sheets

(51) Int. Cl.
*A61N 1/375* (2006.01)
*H01R 13/639* (2006.01)
*H01R 13/645* (2006.01)
*A61N 1/05* (2006.01)
*H01R 24/84* (2011.01)

(52) U.S. Cl.
CPC ....... *H01R 13/639* (2013.01); *H01R 13/6456* (2013.01); *A61N 1/05* (2013.01); *H01R 24/84* (2013.01); *H01R 2201/12* (2013.01)

(56) References Cited

U.S. PATENT DOCUMENTS

| | | | | |
|---|---|---|---|---|
| 5,123,849 | A * | 6/1992 | Deak | H01R 12/57 439/591 |
| 5,755,743 | A * | 5/1998 | Volz | A61N 1/3754 607/36 |
| 6,198,969 | B1 * | 3/2001 | Kuzma | A61N 1/3752 607/37 |
| 6,321,126 | B1 | 11/2001 | Kuzma | |
| 7,445,528 | B1 | 11/2008 | Kuzma | |
| 7,534,127 | B2 * | 5/2009 | Parker | A61N 1/36036 439/425 |
| 7,794,256 | B1 * | 9/2010 | Sochor | H01R 13/025 439/289 |
| 8,412,330 | B2 * | 4/2013 | Kast | H01R 13/5224 607/37 |
| 2005/0118887 | A1 | 6/2005 | Hoffer et al. | |
| 2010/0042169 | A1 | 2/2010 | Barker | |

OTHER PUBLICATIONS

English translation of the International Preliminary Report on Patentability with Written Opinion issued for corresponding International Application No. PCT/EP2015/075286 dated May 2, 2017.
Examination Report for corresponding German Patent Application No. 10 2014 115 859.8 dated Jul. 1, 2015 with an English translation.

* cited by examiner

IMPLANTABLE PLUG CONNECTOR

CROSS REFERENCE TO RELATED APPLICATIONS

This application is a continuation of International Application No. PCT/EP2015/075286, filed on Oct. 30, 2015, which takes priority from German Patent Application No. 10 2014 115 859.8, the contents of each of which are incorporated by reference herein.

TECHNICAL FIELD

The present invention relates to an implantable plug connector.

BACKGROUND

Active implants (Active Implantable Medical Devices=AIMDs) have been well established in modern medical therapy options. Usually, active implants are composed of the two basic modules, stimulation unit and electrodes, which are connected to each other via cables. These, however, sometimes are lying far apart from each other, because in the immediate effective area of the implant, there is not enough space for the stimulator.

Thus, the stimulator is placed, e.g., with respect to neurostimulators, in the chest area within a skin fold; cables running from the chest up to the skull via the neck connect it to the electrodes in the brain. While former AIMD systems were made so to say "from one cast", thus, stimulation unit, cables, and electrodes were connected to each other fixedly, nowadays, multi-piece configurations are prevailing. At first, the parts are implanted individually. The electrical connection of the individual parts is carried out subsequently. For this, an implantable plug connector is required. The latter may, as it is common with respect to cardiac pacemakers, be placed directly at the housing of the stimulator, or, as for example with respect to neuroprostheses, within the cable area between the components. The latter, however, is only applied for up to four channels, and thus, very "slim" plug connectors; in contrast, variants with more channels are placed directly at the stimulator.

Further developments lead to systems which are becoming continuously smaller with complex stimulation and detection functions. This is closely accompanied by a steady increase of the channel number for more selective stimulation. By this, also the requirements on the plug connector increase, which ensures the forwarding of the signals.

Known electrical plug connectors are configured according to the plug-socket-principle ("male"-"female"-principle). Hereby, the male part is formed by one or more pins, which are inserted into corresponding sockets of the female part in the assembled state. The pins of the male part also project beyond the surface, which supports the pins. It is possible that dirt accumulates at the pins and at the sockets during the implantation in a pre-assembled state.

It is an object to provide an implantable plug connector, according to which this is avoided at least partially.

SUMMARY

This object is solved by an implantable plug connector according to claim 1, and a manufacturing method according to the independent method claim. Preferred embodiments are defined in the dependent claims.

Accordingly, an implantable plug connector according to the invention is provided, comprising:

an inner portion comprising a number of contact surfaces, which are embedded at least partially in a surface of a first substrate, an outer portion, comprising a number of contact surfaces, which are embedded at least partially in a surface of a second substrate, wherein the outer portion defines a space, in which the inner portion is receivable in an assembled state, wherein the contact surfaces, in a pre-assembled state, are set back with respect to the surface of the respective substrate, and wherein, in an assembled state, the inner portion is pressed against the outer portion such that contact surfaces corresponding to each other contact each other.

Because the contact surfaces are set back with respect to the surface, in which they are embedded, the dirt of the contacts during the implantation, as it is common with respect to the known plug connectors, can be avoided better. Thus, a "female-female" connection is concerned, because both contacts corresponding to each other, in the pre-assembled state, respectively are set back with respect to the surface, in which they are embedded. Thus, they are located in recesses within the respective substrate. During assembly, the inner portion and the outer portion are pressed against each other such that the contact surfaces reach the surface, and then, contact surfaces facing each other pairwise and the plug connector therefore becomes electrically conductive.

The inner portion, thus, forms a part of the implantable plug connector, and the outer portion forms the other part of the implantable plug connector. In the assembled state, both parts are jointed.

The inner portion also comprises a first substrate, and the outer portion thus comprises the second substrate.

The pressing onto each other of the two portions may be effected by electrically insulating adjacent contact surfaces.

If the contact surfaces are structured at least partially, the contact is more safely ensured in the assembled state. Comb-shaped, convex indentations have been found to be particularly advantageous.

By pressing the two portions onto each other in the assembled state, the contact surfaces can be sealed against the space. This means that the contact surfaces do not come into contact with body fluids from the surroundings.

The outer portion may comprise at least two housing parts having respectively predetermined depths, which define the space in the assembled state. The housing parts may be symmetrical to each other; thus, housing halves (half shells) may be involved.

Hereby, at least one of the housing parts, preferably both housing parts of the outer portion, may comprise a surface with embedded contact surfaces.

In the pre-assembled state, the sum of the depths of the housing parts may be less than the height of the inner portion. With this, it is ensured in a most simple manner that during joining the housing parts, pressure is applied to the inner part, and the contact surfaces contact each other.

The plug connector may further comprise: a screw connection, by means of which the inner portion, in the assembled state, is pressed against the outer portion. A screw connection (screw and threaded hole) is particularly well suited—even if not the only option—to achieve the contact pressure in the assembled state.

The plug connector further may comprise a channel in axial direction, which enables the insertion of a guide wire. The axial direction is an imaginary line between those points, at which the cables penetrate the respective ends of the plug connector. The guide wire is required, in order to insert the respective parts during surgery respectively into the human (or animal) body.

In order to prevent the guide wire from being forgotten within the body, the channel may be blocked in the assembled state by means of the screw connection. The screws, thus, cannot be screwed in without having removed the guide wire previously.

Further, contact zones may be provided, which on the one hand may be connected to wires, and on the other hand, to the contact surfaces.

Further, reverse polarity protection means may be provided, which ensure, in the assembled state, that the inner portion is receivable within the outer portion according to exactly one orientation with respect to the outer portion. This achieves an unequivocal relative orientation of the inner part and outer part, and thereby, an unequivocal assignment of the contact surfaces with respect to each other.

The outer portion and/or the inner portion may be cast with silicone.

In particular metal, preferably titanium, is employed as material for the outer portion or parts thereof.

The invention also comprises a method for manufacturing of contact surfaces for a plug connector, in particular, for a plug connector according to the invention, comprising the steps of:
  spin-coating of a first silicone layer on a ceramic substrate;
  roll-coating of metal;
  structuring of the roll-coated metal for forming conductor paths;
  spin-coating of a second silicone layer;
  exposing of the contact surfaces.

The structuring preferably is effected by a picosecond laser.

The exposed contact surfaces may be structured, preferably, by means of a nanosecond laser.

BRIEF DESCRIPTION OF THE DRAWINGS

The invention is described by means of embodiments and the drawing in more detail. In the drawing.

DETAILED DESCRIPTION

Figure 1:
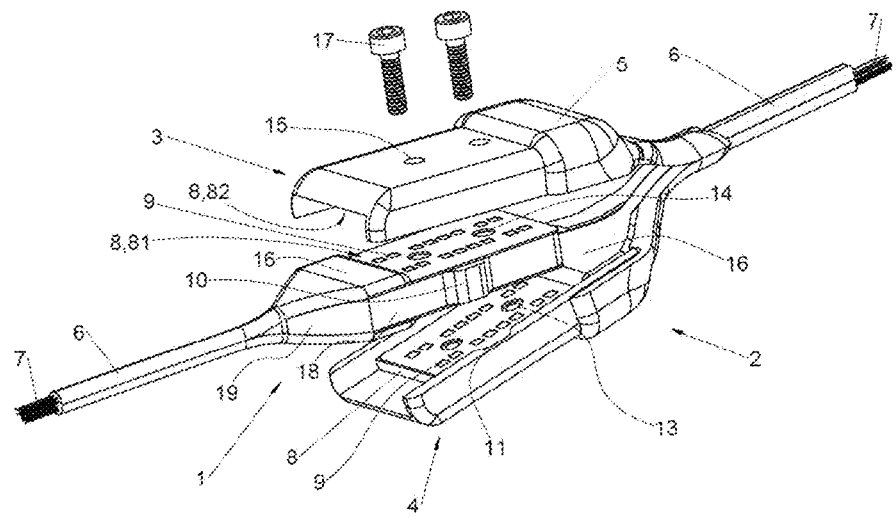
FIG. 1 shows an embodiment of the plug connector according to the invention in a pre-assembled state.
Figure 2:
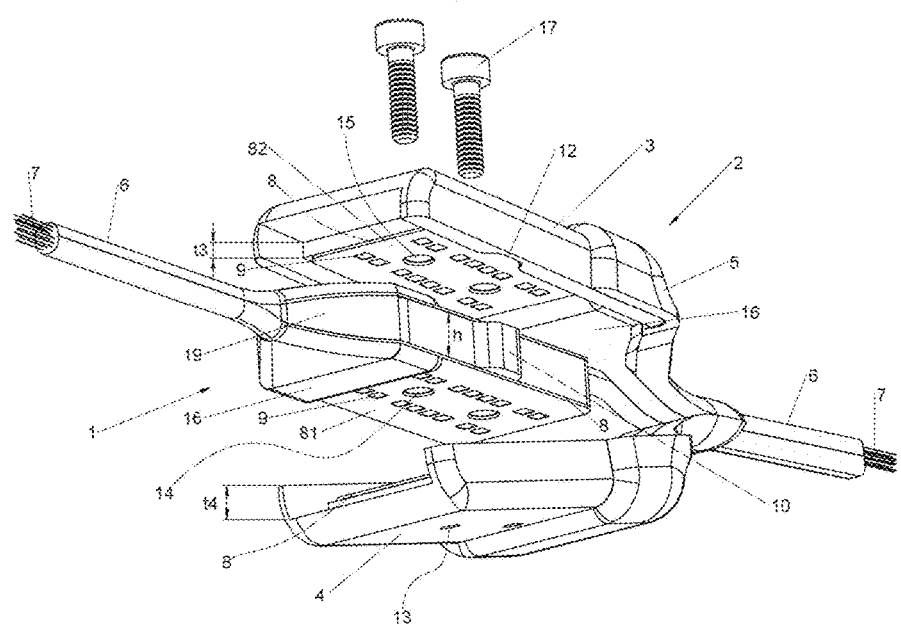
FIG. 2 shows the plug connector of the embodiment from another perspective.

FIG. 1 to FIG. 4 show an embodiment of the implantable plug connector according to the invention. The implantable plug connector comprises: an inner portion 1, comprising a number of contact surfaces 9, which are embedded in a surface 81 of a first substrate 8 at least partially, an outer portion 2, comprising a number of contact surfaces 9, which are embedded in a surface 82 of a second substrate 8, wherein the outer portion defines a space, in which the inner portion is receivable in an assembled state, wherein the contact surfaces 9 are set back with respect to the respective surface 81, 82 of the respective substrate 8 in a pre-assembled state, and wherein, in an assembled state, the inner portion 1 is pressed against the outer portion 2 such that contact surfaces 9 corresponding to each other contact each other.

The inner portion 1 thus comprises the first substrate 8, and the outer portion 2 thus comprises the second substrate 8.

The term "pre-assembled state" means the state at the end of the manufacturing process of the inner portion and the outer portion. The term "assembled state" means the state after insertion of the inner portion into the outer portion and fixation of the inner portion in the outer portion. Then, contact surfaces 9 corresponding to each other contact each other pairwise, i.e., the plug connector is electrically connected.

The outer portion 2 comprises two housing parts 3, 4. At the ends of the inner portion 1 and the outer portion 2, cables 6 are arranged, which in turn comprise wires 7. The cables 6 are connected to the respective contact surfaces 9 via contact zones 16, which are arranged at the ends of the inner portion 1 and the outer portion 2. The two housing parts 3, 4 and the outer portion 2 respectively comprise a number of contact surfaces 9 in respectively one surface 82.

The plug connector according to this embodiment is configured as 32-pole. In order to save space, the contact surfaces 9 of the outer portion 2 are distributed on two surfaces 82 with respective contact surfaces 9, wherein the 16 contact surfaces of each surface 82 are further disposed in two rows à 8 contact surfaces 9. After closing of the plug connection, namely, in the assembled state, two "arms" (namely, the housing parts 3, 4) of the outer portion 2 embrace an inner portion 1 provided with contact surfaces 9 on both sides (namely, in the figure at the top side and the bottom side).

The electrical contact is realized via the contact surfaces 9 (planar pads). Thereby, platinum-iridium structures embedded into the substrate 8 made from silicone are involved. The contact surfaces (pads) 9 thus arranged provide the advantage that they can be cleaned during surgery easier with little residue than, for example, pins and sockets.

A further advantage of this assembly is that for manufacturing, processes specific for implantable electrodes may be employed.

The locking mechanism 13, 17 comprises one or more screws 17, which respectively are screwed through a through hole 15 in a housing part 3, and through a through hole 14 in the inner portion into a threaded hole 13 of the other housing part 4. The screw connection offers the possibility to ensure the contact pressure necessary for a reliable contact by means of the definition of torque values. The screws 17 may be tightened by an operator by means of disposable torque screw drivers supplied therewith, and ensure the mechanical (and thereby also the electrical) connection.

The silicone substrates (silicon mats) 8, in which the conductive paths and contact surfaces (pads) 9 are located, are disposed embedded within troughs with respect to the outer portion 2, which are formed by the housing parts 3, 4. The troughs or the housing parts 3, 4 are made from metal, preferably, titanium is used for this. The outer portion 2 is formed mechanically rigid, in order to distribute the force applied by means of the screws 17 evenly over the surfaces 82 comprising the contact surfaces 9, and to minimize possibly occurring deflections.

Due to the encapsulation with the outer portion 2, for the inner portion 1, the use of metal as substrate may be omitted. Polyetheretherketon (PEEK) or e.g., any other biostable plastic material with high rigidity may be used.

Figure 3:
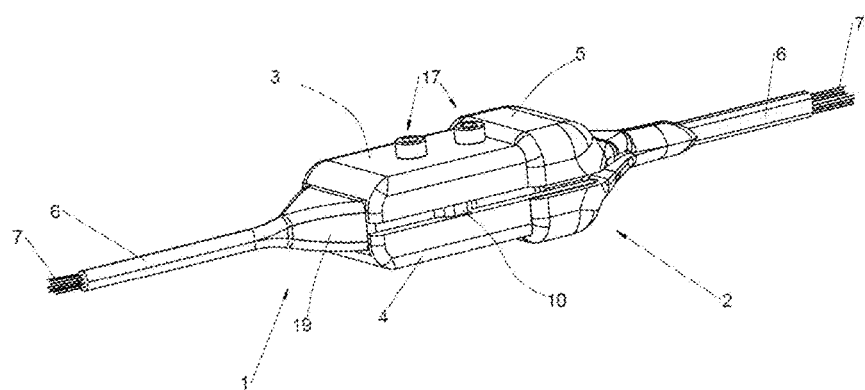
FIG. 3 shows the plug connector in an assembled state.
Figure 4:
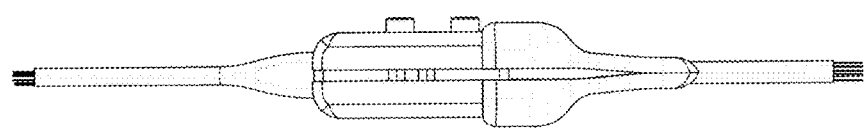
FIG. 4 shows the plug connector in the assembled state in a side view.

The inner portion 1 has a slightly greater height h than the sum of the depths t3+t4 of the two housing parts 3, 4 of the outer portion 2, and therefore, during closing (in the assembled state), it is not completely enclosed, cf. FIG. 3 and FIG. 4. A small gap between the two housing parts 3 and 4 remains. Thereby, it is ensured that the contact pressure in fact is applied to the substrates 8 with the contact surfaces 9, and is not, for example, absorbed by the edges of the housing parts 3, 4.

In the embodiment, each housing part 3, 4 respectively comprises a second substrate 8 with contact surfaces 9 in the respective surface 82. Accordingly, the inner portion comprises contact surfaces 9 corresponding to each other on two faces in respectively one surface 81 of a first substrate 8.

The contact surfaces 9, however, do not have to be respectively distributed on both surfaces 81 of the inner portion 1, the invention also encompasses the case that the inner portion 1 only comprises contact surfaces 9 on the one side, e.g., on the top side, and accordingly also the outer portion 2 only comprises contact surfaces 9 at the surface of the corresponding housing part 3 or 4.

The transition from the cables 6 to the plug connector is formed by casting in silicone. The sensitive connection area (the contact zone) 16 thus is relieved from mechanical strain, and the electrical contacts are supported and insulated towards the outside. The housing parts 3, 4 are cast with silicone such that they take the positions of the assembled state (namely, in the closed state) easier. The silicone cast 5 facilitates the screwing of the system. The electrical connection of the wires to the terminals of the plug connector is carried out by laser welding. A silicone cast 19 of the silicone mats and the substrate of the inner portion 1 is provided in a similar manner.

An asymmetrical shape of the inner portion 1 and the counterparts of the outer portion 2 acting as reverse polarity protection means 10 ensures reverse polarity protection of the plug connector. In the embodiment, the reverse polarity protection means 10, 11, 12 comprise an indentation 11, 12 in one section, as well as a mating indentation 10 in the other section.

The edges at the front side of the inner part 1 are provided with chamfers, whereby the housing parts 3, 4 are pressed apart from each other upon insertion of the inner portion 1.

Because the plug connector according to the invention is of an "In-line" design, namely, the surfaces 81, 82 with the contact surfaces 9 are oriented along the longitudinal axis of the plug connector, it is also compatible to guide wires. The channel running through the inner portion 1 provided for this intersects the screw holes 14, thus, an insertion of a guide wire is only possible if the plug connector is not screwed together. This offers the possibility of avoiding errors during the procedure of surgery.

FIGS. 7a-7j show method steps for creating the contact surfaces. Hereby, silicone and metal foils are stacked on top of each other in an alternating manner, and are structured by means of laser. The method steps for the contact surfaces:
 a-c) spin-coating of silicone and structuring, if needed;
 d-f) roll-coating, structuring and removing of metal;
 g-i) embedding into silicone and opening of the contacts;
 j) lifting of the layer composite.

Figure 7A:
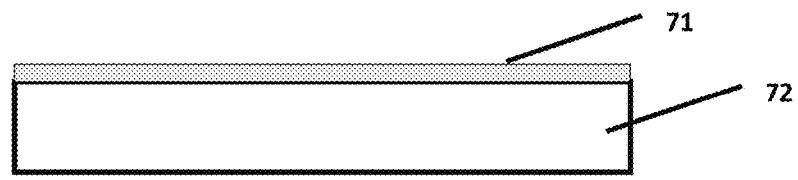
FIGS. 7a-7j show manufacturing steps of the contact surfaces in the substrate.
Figure 7B:
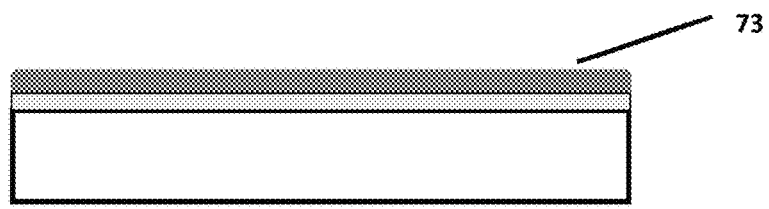
Figure 7C:
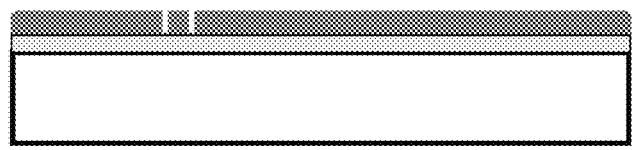

In detail:

At first, an $Al_2O_3$ ceramic substrate 72 is laminated with PVC adhesive tape 71 (FIG. 7a). On top of this, a first layer of silicone 73 is spin-coated. The layer thickness of this layer may be about 30 μm at a rotational speed of 2000 rpm for 90 s up to about 70 μm at 500 rpm for 90 s (FIG. 7b). Depending on the process, the silicone layer is still cut by means of laser, in order to be able to expose the metal later on also from the rear side (FIG. 7c). This double-sided contacting is necessary, if the connection wires are to be connected to the probes by means of laser welding, or with respect to folding of the silicone mats.

Figure 7D:
Figure 7E:
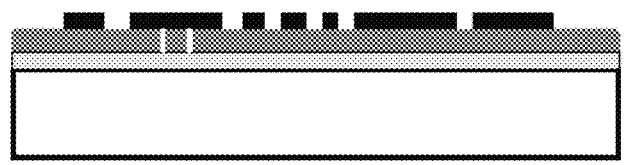
Figure 7F:
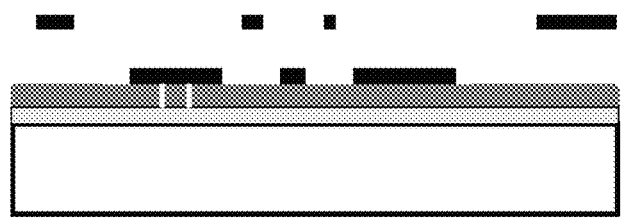

Subsequently, metal foil 74 is rolled-on, is structured by means of laser, and the areas are removed between the conductive paths (FIG. 7d-f).

Figure 7G:
Figure 7H:
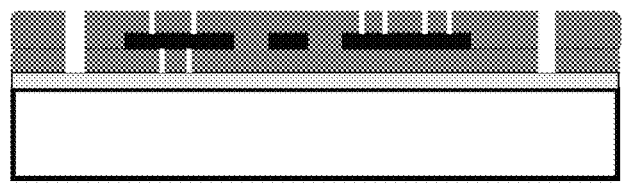
Figure 7I:
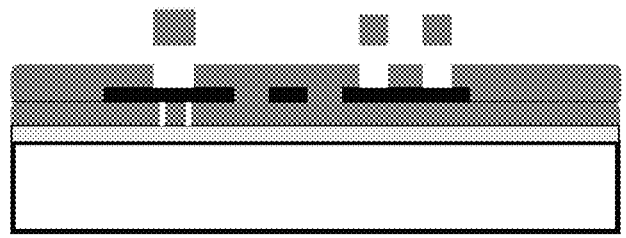

A second silicone layer 75 about of about 32 μm thickness is spin-coated with 4000 rpm for 90 s and cured (FIG. 7g). The contact areas are exposed by cutting their contours by means of laser into the silicone, and by withdrawing the excessive silicone by means of a tweezer (FIGS. 7h, 7i).

Figure 7J:
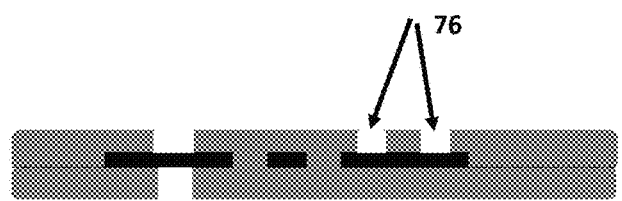

In the last laser step, the contour of the contact pad array 76 is cut out. The finished layer composite then is removed, if needed, with the addition of ethanol, from the substrate (FIG. 7j).

In order to release residue from the contact surfaces 9, the probes are cleaned with ethanol and DI-water.

In order to be able to apply the silicone by means of spin-coating, it is diluted previously in a ratio of 1:1 with n-heptane.

As material for the contact surfaces 9, PtIr-foil (90% platinum, 10% iridium), 25 μm thick, may be used.

Preferably, a laser having pulse widths on a picoseconds scale ("picosecond laser") is used. Pulse widths on the picoseconds scale enable a more precise and more selective structuring than e.g., pulse widths on a nanoseconds scale ("nanosecond laser"). An Nd:YVO4-laser may be employed as laser.

A further advantage of the picosecond laser is the higher reproducibility concerning the alignment of the surfaces. With respect to a nanosecond laser, multiple taking out and putting back in often leads to a displacement between the lasered structures.

Surprisingly, it has been found that the selection of the laser for structuring the surface of the contact surfaces 9 affects the formation of the electrical contact.

Preferably, the contact surfaces (FIG. 7d-f) are also formed from PtIr by means of the picosecond laser. Subsequently, the exposed metal surfaces are structured by means of the nanosecond laser. This additional step aims at the targeted generation of material throw-ups by means of melting. Such elevations of the otherwise plane contact surfaces contribute to the contact formation.

The pattern for this structuring or the density of the material throw-ups thus affects the contact formation. For this, the number of the steps using the nanosecond laser may be varied. The steps, preferably, are aligned diagonally such that they intersect upon putting the contact surfaces 9 on top of each other (namely, in the assembled state). Preferably, several steps (e.g., seven steps respectively) are applied per contact surface.

Figure 5A:
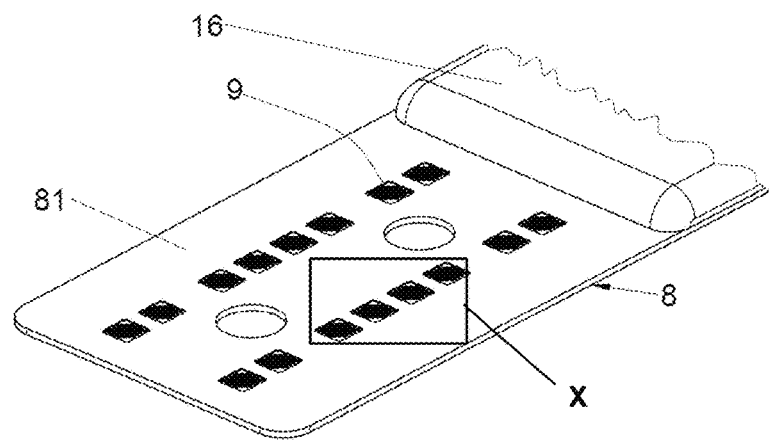
FIGS. 5a and 5b show a substrate with the contact surfaces and the contact zone.
Figure 5B:
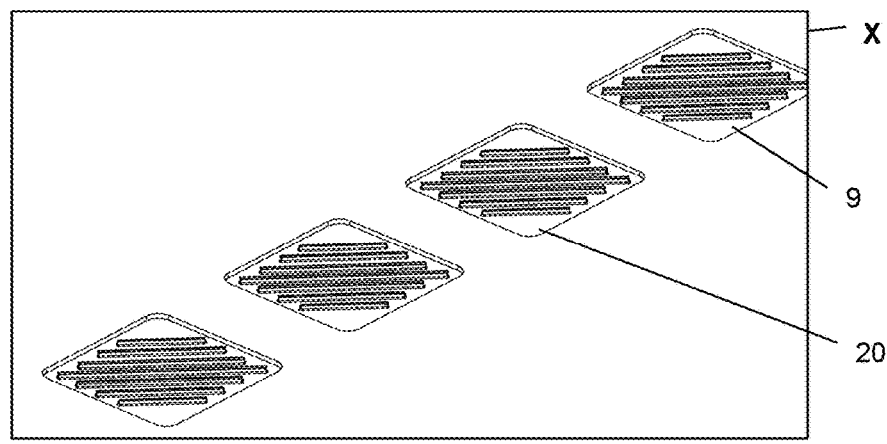

FIGS. 5a and 5b show a substrate 81, 82 with the contact surfaces 9. The contact surfaces are provided with three-dimensional structures 20. These structures 20 are formed as diagonal grooves which intersect upon contact of the respective contact surfaces 9.

Figure 8:
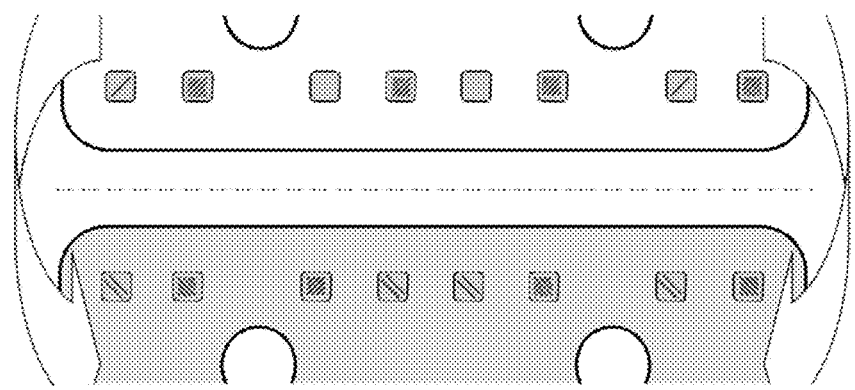
FIG. 8 shows examples for surface structures of contact surfaces.

FIG. 8 shows further patterns for the three-dimensional structures.

Figure 6A:
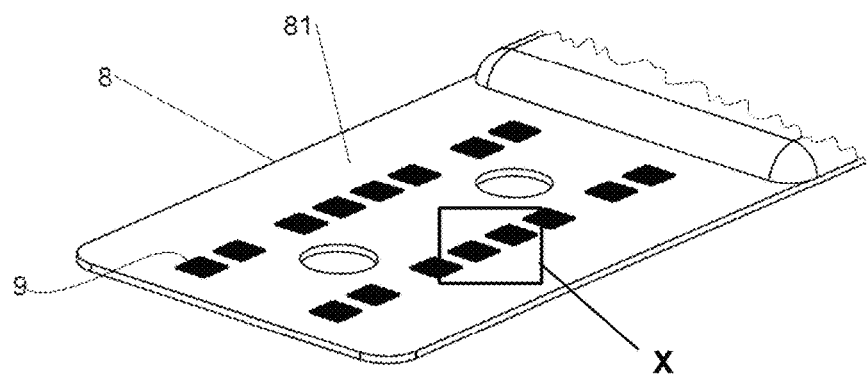
FIGS. 6a and 6b show the contact surfaces set back in the substrate.
Figure 6B:
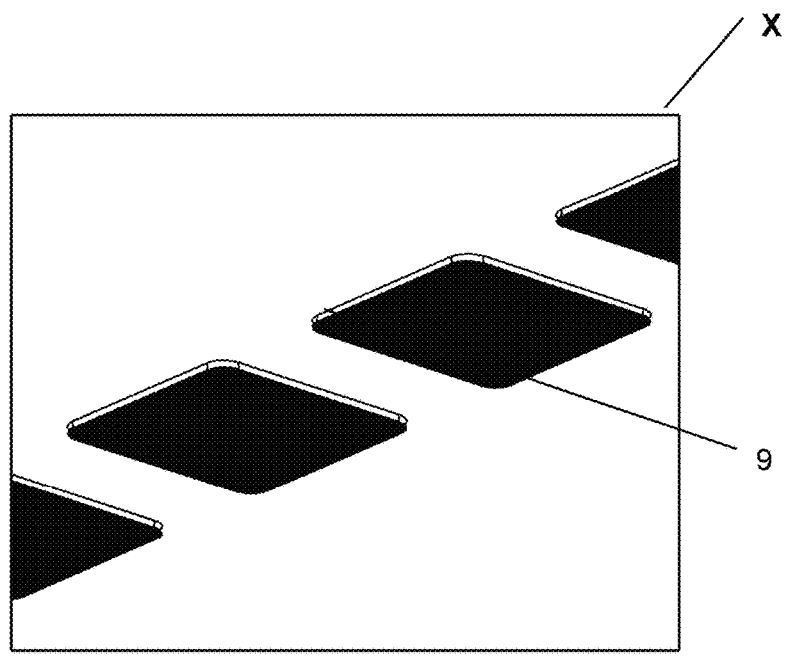

FIGS. 6a and 6b show the arrangement of the contact surfaces 9 in relation to the surfaces 81, 82. As can be seen here, the contact surfaces 9 are embedded in the surfaces, are positioned in a set back manner, namely, slightly deeper than the surfaces 81, 82. The contact surfaces are located at a greater depth which approximately corresponds to the depth of the second silicone layer (in the embodiment (about 32 μm)) deeper.

Figure 9:
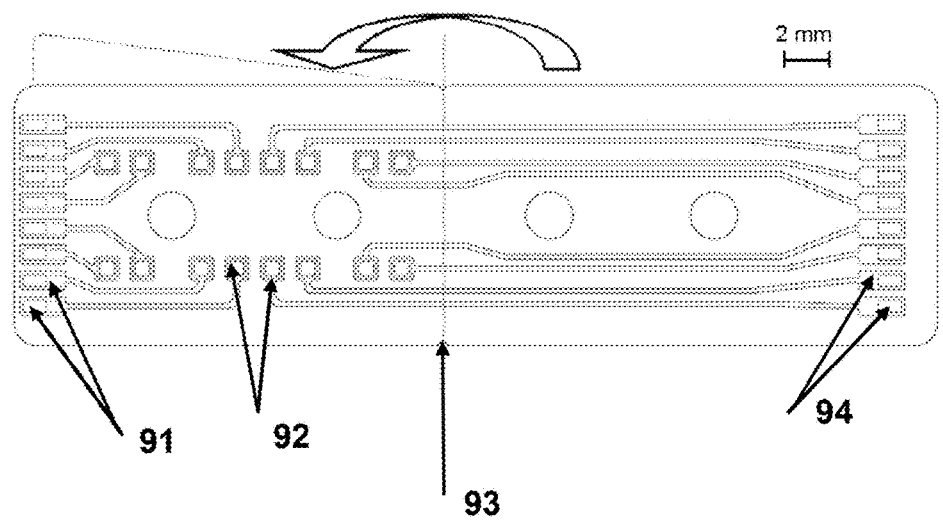
FIG. 9 shows the design of the contact zone and of the contact surfaces.

The contact openings at the contact zone 16 and the conductive paths to the contact surfaces 9 are a limiting factor for the number of the channels which may be realized on the substrate. In order to be able to increase the number of contact surfaces 9, the silicone substrate may be folded together with the contact surfaces 9 (the silicon mats 8) one time. This increases the conductive path density and serves for minimizing the dimensions of the plug connector. This is illustrated in FIG. 9. In order to connect the folded silicone mats to each other, their surfaces are plasma activated prior to joining.

60 μm thick wires 7 which are guided through a 1.8 mm thick silicone tube are used. For the connection of the two outer parts of the plug connector, a cable, which is distributed from 1×32 channels to 2×16 channels, is used.

The cables 6 may be soldered on the contact points of the silicone substrate (of the silicone mats) 8, and the solder joints may be cast with silicone.

The contact substrates 81, 82 may be fixed on the housing parts by means of silicone adhesive. Subsequently to this, also the entire transition zone between the cable and the plug may be cast by means of Teflon molds. In order to minimize bubble formation, the silicone may be cured under an overpressure of 1.2 bars at 100° C.

In the assembled state, the two "arms", namely, the two housing parts 3, 4 of the plug connector are jointed. For this, the plug connector at first is closed and fixed by means of screws in order to make the external parts preferably take a closed position after adhering.

By joining the two housing parts 3, 4, the inner part 1, namely, the silicone substrate 8, is pressed against the housing parts or the substrates arranged therein. Because the height hl of the inner part is slightly higher than the sum of the depths t3, t4 of the housing parts and the silicone substrates 8 cannot escape from the space, the substrates 8 press the set-back contact surfaces 9 into the air gap respectively lying above, which is easily compressible, until contact surfaces 9 corresponding to each other (opposing) contact each other pair-wise.

Because the silicone substrate is flexible, this procedure is reversible for an arbitrary number of times. The plug connector may be opened by releasing the screw connection 17 any number of times, namely, the mechanical and electrical connection is disconnected, and is closed again repeatedly.

LIST OF REFERENCE NUMERALS 1 inner portion
2 outer portion
3, 4 housing part
5 silicone cast of the outer shells and silicone mat
6 multi-channel cable
7 conductors/wires/veins
8 first substrate, second substrate (polymer/rubber mat)
9 contact surfaces, contact pads
10 indentation as reverse polarity protection means
11, 12 indentation/recess as reverse polarity protection means
13 threaded hole for screw
14, 15 through-hole for screw
16 contact zone/terminals for cable
17 screw
18 substrate inner part
19 silicone cast of silicone mats and substrate of inner part
20 3D-structuring of the contact surface
71 adhesive tape
72 ceramic substrate
73 1st layer of silicone
74 metal foil
75 2nd layer of silicone
76 contact pads
81 surface of the first substrate
82 surface of the second substrate
91 front side openings
92 contact pads
93 fold
94 rear side openings
h height of the inner part 1
t3 trough depth of the first housing part 3
t4 trough depth of the second housing part 4

What is claimed is:

1. An implantable plug connector, comprising:
    an inner portion (1), comprising a number of contact surfaces (9), which are embedded in at least one surface (81) of a first substrate (8),
    an outer portion (2), comprising a number of contact surfaces (9), which are embedded in at least one surface (82) of a second substrate (8),
    wherein the outer portion (2) defines a space, in which the inner portion (1) is receivable in an assembled state,
    wherein the contact surfaces (9) embedded in the at least one surface of the first substrate and the contact surfaces embedded in the at least one surface of the second substrate, in pre-assembled state, are set back with respect to the corresponding surface (81, 82) of the respective substrate (8),
    and wherein, in the assembled state, the inner portion (1) is pressed against the outer portion (2) such that contact surfaces (9) corresponding to each other contact each other.

2. The implantable plug connector of claim 1, wherein the contact surfaces (9) embedded in the at least one surface of the first substrate and the contact surfaces embedded in the at least one surface of the second substrate are structured locally.

3. The implantable plug connector of claim 1, wherein, in the assembled state, adjacent contact surfaces (9) on the at least one surface of the first substrate and the at least one surface of the second substrate are electrically insulated with respect to each other.

4. The implantable plug connector of claim 1, wherein, in the assembled state, the contact surfaces (9) are sealed against the space.

5. The implantable plug connector of claim 1, wherein the outer portion (2) comprises at least two housing parts (3, 4) having respectively predetermined depths (t3, t4), which, in the assembled state, define the space.

6. The implantable plug connector of claim 5, wherein each one of the housing parts (3, 4) respectively comprises a number of contact surfaces (9) in respectively one surface (82).

7. The implantable plug connector of claim 1, wherein, in the pre-assembled state, the sum of the depths (t3, t4) of the housing parts is lower than the height (h1) of the inner portion (1).

8. The implantable plug connector of claim 1 further comprising: a screw connection (13, 17), by means of which, in the assembled state, the inner portion (1) is pressed against the outer portion (2).

9. The implantable plug connector of claim 1 further comprising: a channel in axial direction enabling an insertion of a guide wire.

10. The implantable plug connector of claim 9, wherein the channel, in the assembled state, is blocked by the screw connection (13, 17).

11. The implantable plug connector of claim 1 further comprising:
   contact zones (16), which are connectable to lines (7) and to the contact surfaces (9).

12. The implantable plug connector of claim 1 further comprising: reverse polarity protection means (10, 11, 12) ensuring, in the assembled state, that the inner portion is received in exactly one orientation with respect to the outer portion within the outer portion.

13. The implantable plug connector of claim 1, wherein the outer portion (2) and/or the inner portion (1) at least partially are cast with silicone.

14. A method for manufacturing contact surfaces for the plug connector of claim 1, comprising:
   spin-coating of a first silicone layer onto a substrate;
   rolling-coating of metal;
   structuring of the rolled-coated metal for forming of conductive paths;
   spin-coating of a second silicone layer;
   exposing of the contact surfaces (9).

15. The method of claim 14, wherein structuring is carried out by means of a picosecond laser.

16. The method of claim 14, wherein the exposed contact surfaces (9) are structured.

* * * * *